United States Patent [19]

Ruffing et al.

[11] 4,341,901

[45] Jul. 27, 1982

[54] 4-ALKYLTHIO-2-TRIFLUOROMETHYLALKANESULFONANILIDES AND DERIVATIVES THEREOF

[75] Inventors: Sharon L. Ruffing, Oakdale; Wallace E. Burg, Lakeland; Ezzat A. Mikhail, New Brighton, all of Minn.

[73] Assignee: Minnesota Mining and Manufacturing Co., Saint Paul, Minn.

[21] Appl. No.: 196,757

[22] Filed: Oct. 14, 1980

Related U.S. Application Data

[63] Continuation-in-part of Ser. No. 879,079, Feb. 21, 1978, abandoned, which is a continuation-in-part of Ser. No. 786,222, Apr. 11, 1977, abandoned.

[51] Int. Cl.³ .................. C07C 143/75; A01N 9/16
[52] U.S. Cl. .................................. 564/99; 71/98; 71/103
[58] Field of Search .................. 564/99; 71/98, 103

[56] References Cited

U.S. PATENT DOCUMENTS

| | | | |
|---|---|---|---|
| 3,639,474 | 2/1972 | Harrington et al. | 71/103 X |
| 3,856,859 | 12/1974 | Moore et al. | 71/103 X |
| 3,981,914 | 9/1976 | Mutsch et al. | 71/103 X |
| 3,996,277 | 12/1976 | Fridinger et al. | 71/103 X |

FOREIGN PATENT DOCUMENTS

1188591 8/1976 France.
971219 11/1973 United Kingdom.

*Primary Examiner*—Thomas A. Waltz
*Attorney, Agent, or Firm*—Cruzan Alexander; Donald M. Sell; Donald C. Gipple

[57] ABSTRACT

2-Trifluoromethylalkanesulfonanilides substituted in the para position by alkylthio, alkylsulfinyl or alkylsulfonyl groups and agriculturally acceptable salts thereof are useful herbicides and plant growth regulators.

26 Claims, No Drawings

4-ALKYLTHIO-2-TRIFLUOROMETHYLALK- ANESULFONANILIDES AND DERIVATIVES THEREOF

This is a continuation-in-part of application Ser. No. 879,079 filed Feb. 21, 1978, now abandoned, which is itself a continuation-in-part of application Ser. No. 786,222, filed Apr. 11, 1977 (now abandoned) with which Ser. No. 879,079 was copending.

BACKGROUND OF THE INVENTION

This invention relates to 2-trifluoromethylalkanesulfonanilides substituted in the para position by alkylthio, alkylsulfinyl or alkylsulfonyl groups and to agriculturally acceptable salts thereof. The compounds of the invention are active plant growth modifying agents. The invention also relates to plant growth modifying compositions comprising the compounds of the invention dispersed in agriculturally acceptable extending media and to the use of the compounds to modify the growth of higher plants. Methods for preparing the compounds and intermediates in their preparation are also included.

Plant growth modification as defined herein consists of all deviations from natural development, for example, defoliation, stimulation, stunting, inhibition, desiccation, tillering, and even death. This plant growth modifying activity is generally observed as the compounds of the invention begin to interfere with certain processes within the plant. If vital processes are affected, the plant will die if treated with a sufficient dose of the compound and the compound can be termed a herbicide relative to that plant. If the plant is a weed, the compound can be used to control or kill it and this is particularly valuable when a compound controls or kills a weed at an application rate that has little or no effect on a crop plant. I.e., it can serve as a selective herbicide to control or kill the weed in the presence of that crop. On the other hand, the growth of desirable plants can sometimes be modified beneficially, e.g., to suppress undesirable growth or to improve the quantity or quality of the harvest from the plant or to serve as a harvest aid. Such beneficial modifications can be termed plant growth regulation.

The compounds of the present invention are broadly active as plant growth modifiers. As such they are plant growth regulators and herbicides and, as will be seen, frequently also serve as selective herbicides.

Both haloalkylsulfonamido-substituted and methylsulfonamido-substituted aromatic compounds have been known heretofore, as have certain uses for these compounds. Thus, U.S. Pat. No. 3,639,474 discloses trifluoromethanesulfonanilides, including such compounds with trifluoromethyl, methylthio, methylsulfinyl and methylsulfonyl substituents, to be useful as herbicides. French Pat. No. 1,188,591 includes disclosures of two classes of compounds, i.e., haloalkylsulfonanilides and haloalkylsulfonamidodiphenyl compounds in which the rings are bonded directly or are linked by various groups including sulfonyl, sulfinyl and thio groups. The areas of utility disclosed by the French patent include activity against textile material parasites as well as antibacterial and anti-mildew activity. Herbicidal activity is not disclosed in that patent however. British Pat. No. 971,219 discloses alkanesulfonanilides containing both chlorine and nitro ring substituents to have herbicidal activity.

U.S. Pat. No. 3,996,277 discloses that 4-methylthio-2-trifluoromethylmethanesulfonanilides (and the methylsulfinyl and methylsulfonyl derivatives thereof) have plant growth regulating activity, and that they are particularly valuable in controlling established rhizomatous johnsongrass (*Sorghum halepense* (*L. Perse.*)), a stubborn weed pest, particularly in the southern United States. Such compounds have, in fact, the particularly valuable selective herbicidal property of controlling rhizomatous johnsongrass at application rates tolerated by cotton. Thus they can be used to control rhizomatous johnsongrass selectively in cotton fields, a unique and extremely valuable characteristic.

The compounds of the present invention, which are structurally similar to those of U.S. Pat. No. 3,996,277, also have this selective activity and in addition have further advantages as selective herbicides relative to degree and kind of activity and/or tolerance with respect to other crops and as plant growth regulators. For example, compounds of the invention are effective in increasing the sucrose yield in sugar cane, in retarding the growth of grass, in controlling tobacco sucker growth and in increasing the sweetness to acidity ratio of citrus.

DETAILED DESCRIPTION OF THE INVENTION

This invention relates to compounds of the formula

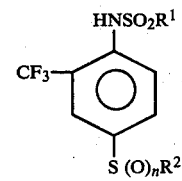

wherein $R^1$ and $R^2$ are independently alkyl groups containing from 1 to 4 carbon atoms and n is 0–2, provided that $R^1$ and $R^2$ are not both methyl, and agriculturally acceptable salts thereof.

The compounds of formula I in which $R^1$ is methyl and $R^2$ is ethyl, in which $R^1$ is ethyl and $R^2$ is methyl, in which both $R^1$ and $R^2$ are ethyl and in which $R^1$ is methyl and $R^2$ is isopropyl constitute preferred subclasses due to their particularly valuable selective herbicidal and plant growth regulating activities.

It is an object of the invention to provide a method for modifying the growth of higher plants, including both plant growth regulating and herbicidal methods (the latter concerning killing or at least controlling the plants), said method comprising contacting the plants with an amount of compound of the invention effective to accomplish the desired result.

It is another object of the invention to provide a selective herbicidal method for killing or at least controlling the growth of a particular weed species in the presence of a specific crop, said method comprising contacting an area containing both types of plants with a concentration of a compound of the invention sufficient to kill or control the weed plants, but insufficient to have any substantial deleterious effect on the crop plants.

It is another object of the invention to provide a method for suppressing the growth of tobacco suckers which comprises applying to growing tobacco plants at an appropriate stage in their development (for example, just after the plants have been topped to remove the main terminal bud) a compound of the present invention in an amount sufficient to accomplish the desired suppression, but insufficient to cause unacceptable damage to the remainder of the plant.

It is another object of the invention to provide a method for increasing the sweetness to acid ratio of citrus fruit which comprises applying to the fruit-bearing branches of a citrus tree at an appropriate time, normally several months prior to harvest, an amount of a compound of the present invention sufficient to bring about the desired result, but insufficient to cause unacceptable damage to the trees.

It is another object of the invention to provide a method for inhibiting the growth of grass which comprises applying to the grass an amount of a compound according to the present invention which is sufficient to bring about the desired result, but insufficient to cause unacceptable damage to the grass.

It is another object of the invention to provide a method for increasing the sucrose yield of sugarcane which comprises applying to the sugarcane an amount of a compound according to the present invention which is sufficient to bring about the desired result.

It is another object of the invention to provide compositions suitable for accomplishing the foregoing objects comprising a compound according to the present invention dispersed in an agriculturally acceptable extending medium.

The term agriculturally acceptable is utilized herein relative to the salts of the invention (in which the H in formula I is replaced by an agriculturally acceptable cation) and also relative to the extending media of the compositions of the invention. This term as utilized also includes "horticulturally acceptable" salts and media which are suitable for non-agricultural uses, for example the treatment of lawns and industrial turfs, etc.

The salts of the invention are generally metal, ammonium and organic amine salts and can be prepared by treating the acid-form compound with an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by cation exchange reaction (by reacting a salt of the invention with an organic or inorganic salt in a cation exchange reaction). The organic amine salts include the salts of aliphatic (e.g. alkyl), aromatic and heterocyclic amines, as well as those having a mixture of these types of structures. The amines useful in preparing the salts of the invention can be primary, secondary or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the alkali metal, alkaline earth, ammonium and amine salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetones, etc. The resulting solution is then treated to remove the solvent, for example, by evaporation under reduced pressure.

The compounds of the invention can be prepared according to the reaction sequences outlined below.

Method 1

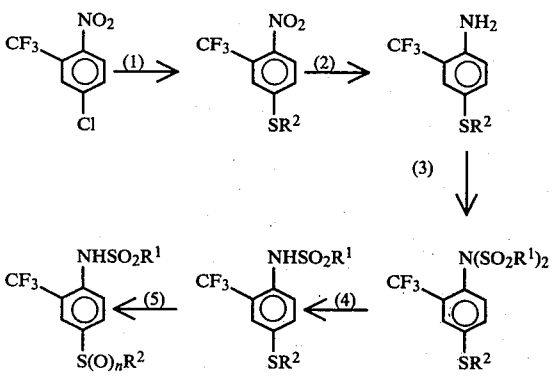

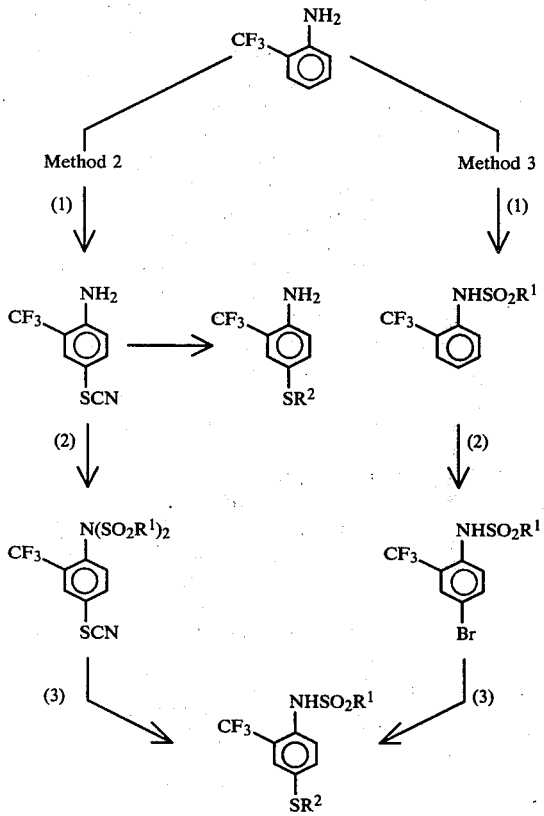

Step (1) of Method 1 is carried out by heating 5-chloro-2-nitrobenzotrifluoride together with a slight excess of an alkanethiol in a suitable solvent in the presence of the appropriate amount of base. The solvent is one in which the reactants are soluble such as a lower alkanol, e.g., ethanol. The base is a strong organic or inorganic base. Suitable organic bases are tertiary amines such as N,N-dimethylaniline, triethylamine, pyridine, alkoxides such as sodium ethoxide and the like. Suitable inorganic bases are alkali metal hydroxides such as sodium and potassium hydroxides, calcium hydride and the like. The product is isolated by conventional methods.

Alternatively, step (1) can be carried out by stirring a methylene chloride solution of 5-chloro-2-nitrobenzotrifluoride and a phase transfer catalyst with an aqueous base solution of the alkanethiol. Other solvents, such as benzene and dichlorobenzene, and various catalysts, such as organic ammonium salts, can also be utilized. Ordinarily the alkanethiol in dilute (approximately 4 percent) aqueous base is reacted with one-half an equivalent of 5-chloro-2-nitrobenzotrifluoride dissolved in methylene chloride in the presence of triethylbenzylammonium chloride (the phase transfer catalyst). However, when a branched thiol, such as 2-propanethiol or 2-methyl-2-butanethiol, is utilized, additional quantities of base and thiol are required for the best yields due to side reaction with the methylene chloride. This phase transfer reaction is ordinarily preferred when mercaptans other than methanethiol are utilized due to substantial amounts of by-products which form in the first-described process (which are frequently difficult to separate from the desired product).

The reaction of step (2) is a reduction of the nitro group of the intermediate 2-nitro-5-alkylthiobenzotrifluoride. Chemical or catalytic methods well known to the art are successful. Raney nickel is one suitable catalyst for the reduction. Product is isolated by conventional methods.

In step (3) of Method 1, the bis(alkylsulfonylation) product is obtained utilizing two or more equivalents of the alkanesulfonyl chloride and excess base. Step (4) is the partial hydrolysis of the intermediate bis(alkylsulfonyl) compounds. This is a high yield base hydrolysis reaction using a strong base such as potassium hydroxide in methanol.

Alternatively the precursor of step (3) can be converted directly to the product of step (4) by means of a mono(alkylsulfonylation) reaction using one equivalent of the alkanesulfonyl chloride and one equivalent of base. Suitable bases for step (3) are inorganic or organic bases such as pyridine, triethylamine, dimethylcyclohexylamine and substituted pyridines.

Step (5) of Method 1 is carried out using conventional oxidation methods such as hydrogen peroxide in acetic acid, sodium metaperiodate and the like. The sulfoxide compound (n=1), is produced when equimolar amounts of the oxidizing agent and the reactant are utilized, whereas the sulfone (n=2) is prepared directly utilizing 2 moles (or a slight excess) of the oxidizing agent per mole of the reactant.

The reaction of step (1) of Method 2 involves the formation of 4-thiocyano-2-trifluoromethylaniline from 2-aminobenzotrifluoride by means of a conventional procedure. Bis(alkylsulfonylation) products are formed in the reaction of step (2) which is carried out utilizing the general procedure and reaction conditions of step (3) of Method 1.

The reaction of step (3) involves the simultaneous partial hydrolysis of the bis(alkylsulfonyl)amido moiety and alkylation of the thiocyano moiety of the N-alkylsulfonyl-4-thiocyano-2-trifluoromethylalkanesulfonanilide to give the 4-alkylthio-2-trifluoromethylalkanesulfonanilide wherein the 4-alkyl group is determined by the alcohol used in the reaction. The conditions under which this reaction is carried out are analogous to those of the hydrolysis reaction of step (4) of Method 1.

It can be seen from the foregoing reaction scheme that 4-alkylthio-2-trifluoromethylanilines can be formed directly from the corresponding 4-thiocyano-2-trifluoromethylaniline which is produced by step (1) of Method 2. This reaction can be carried out utilizing various conventional techniques. For example the thiocyano moiety can be alkylated in an alcoholic sodium cyanide solution. In this reaction the alcohol determines the alkyl group. Alternatively, a sodium mercaptide can be first formed from the thiocyano moiety and it can then be alkylated utilizing an alkylating agent such as an alkyl iodide (methyl iodide). The resulting compound is the same as the product of step (2) of Method 1 and can, of course, be further processed by the procedures of Method 1.

Step (1) of Method 3 is carried out utilizing procedures identical with those of steps (3) and (4) of Method 1. Alternatively, this can be carried out in a single step, as noted previously in discussing steps (3) and (4) of Method 1. The bromination of the 4 position of the ring and the reaction to replace the 4-bromine atom by the 4-alkylthio moiety (steps (2) and (3) of Method 3) are accomplished utilizing known procedures. For example, bromine can be added to a stirred solution of the 2-trifluoromethylalkanesulfonanilide in a water-alcohol solvent, and the thioalkylation step can be carried out by heating a mixture of cuprous thioalkoxide, the 4-bromo compound, pyridine and quinoline, and thereafter pouring it into a 12 N hydrochloric acid-wet ice mixture and the desired product recovered therefrom, e.g. by extraction, distillation and/or recrystallization techniques.

The formula shown as the final product of Methods 2 and 3 represents the 4-alkylthio compounds of the invention which can, if desired, be converted to the corresponding 4-alkylsulfinyl or 4-alkylsulfonyl compounds, as shown in Method 1.

Herbicidal and plant growth regulating activities of the compounds of the invention can be determined using screening tests against selected greenhouse plantings. Both greenhouse tests and field tests are provided in the example section of this specification.

As noted previously, the compounds of the invention have been found to be particularly effective in controlling established rhizomatous johnsongrass (*Sorghum halepense* (*L. Pers.*)). The control of rhizomatous johnsongrass is especially important since it is not ordinarily controlled effectively at an application rate that is tolerant to crops by commercially available herbicides (although seedling johnsongrass is susceptible to several commercial herbicides).

Other important accomplishments of the invention include, as previously mentioned, increasing the sucrose yield in sugar cane and retarding the growth of grass (which is valuable since it reduces the number of times the grass must be mowed). In the former, the compound is applied, usually at a rate of about 0.1 to 2 pounds of active ingredient per acre at from about 3 to 12 weeks prior to harvesting the cane. In the latter, activity is obtained at rates as low as 1/30 pound of active ingredient per acre on growing plants. The maximum application on grass depends upon the sensitivity of the grass under the particular conditions. For reasons of economy, the lowest effective rate is chosen, usually from about 0.1 to 3 pounds of active ingredient per acre. For most grasses as low as one pound per acre is effective.

For application to plants, the compounds can be finely devided and suspended in any of the usual aqueous media. In addition, spreading agents, wetting agents, sticking agents or other adjuvants can be added as desired. Dry powders, as such or diluted with inert materials such as diatomaceous earth, can likewise be used as dusts for this purpose. The preparations are coated on the plants or the ground is covered when pre-emergence control is desired. Application is made with the usual sprayers, dust guns and the like. Application rates are at 0.5 to 20 lbs/acre in general, but may be increased or reduced according to individual circumstances of use.

Since certain compounds of the invention are particularly active against rhizomatous johnsongrass, it can be particularly advantageous to combine them with other known herbicides to broaden or maximize the weed spectrum controlled by herbicidal compositions of this invention or to better control a weed not well controlled by specific compounds of the invention. Among these other known herbicides are phenoxy herbicides, e.g. 2,4-D, 2,4,5-T, Silver and the like, carbamate herbicides, thiocarbamate and dithiocarbamate herbicides, substituted urea herbicides, e.g. diuron, monuron and the like, triazine herbicides, e.g. simazine and atrazine, chloroacetamide and chlorinated aliphatic acid herbicides, chlorinated benzoic and phenylacetic acid herbicides such as chloramben and other herbicides such as trifluralin, paraquat, nitralin and the like. Furthermore, herbicidal compositions containing compounds of the invention may contain, in addition, nematicides, fungicides, insecticides, fertilizers, trace metals, soil conditioners, plant growth regulators and the like. Such combinations are clearly envisioned in this invention.

The following examples are given for the purpose of further illustrating the present invention but are not intended, in any way, to be limiting on the scope thereof. All parts are given by weight unless otherwise specifically noted.

EXAMPLE 1

2-Nitro-5-ethylthiobenzotrifluoride

A solution of 5-chloro-2-nitrobenzotrifluoride (150 g., 0.67 mole) and benzyltriethylammonium chloride (15 g., 0.067 mole) phase transfer catalyst in methylene chloride (1500 ml) is added to a cold (0°–5° C.) stirred solution of sodium hydroxide (53.2 g., 1.33 moles) and ethanethiol (97.47 g., 1.57 moles) in water (1200 ml) over a 1.5-2 hour period. The reaction mixture is allowed to come to room temperature and is stirred for 17 hours. Thin layer chromatography on silica gel with 10 percent ether-90 percent petroleum ether (b.p. 30°–60° C.) diluent indicates all of the 5-chloro-2-nitrobenzotrifluoride has reacted. The methylene chloride layer is then separated from the aqueous layer and washed with water. The methylene chloride is removed by evaporation leaving 2-nitro-5-ethylthiobenzotrifluoride as an oil.

Additional compounds prepared using the same general method are as follows:
2-nitro-5-isopropylthiobenzotrifluoride, an oil.
2-nitro-5-tert-butylthiobenzotrifluoride, an oil.
2-Nitro-5-ethylthiobenzotrifluoride is prepared utilizing the general method of Example 1 of U.S. Pat. No. 3,996,277.

EXAMPLE 2

4-Ethylthio-2-trifluoromethylaniline

A solution of 64 percent aqueous hydrazine (75.6 g., 1.5 moles) is added dropwise to a warm (50° C.) stirred mixture of 2-nitro-5-ethylthiobenzotrifluoride (168.3 g, 0.67 mole) and 5 percent palladium on carbon catalyst (14.5 g) in 95 percent ethanol (1200 ml). After all of the hydrazine has been added, the reaction mixture is heated under reflux overnight. Thin layer chromatography indicates all of the nitro compound is reduced. The reaction mixture is then filtered and concentrated under reduced pressure. The residual golden colored liquid is taken up in methylene chloride and washed with water. The methylene chloride is removed by evaporation leaving the product, 4-ethylthio-2-trifluoromethylaniline.

Additional compounds prepared utilizing the same general method are as follows:
4-isopropylthio-2-trifluoromethylaniline, an oil
4-tert-butylthio-2-trifluoromethylaniline, m.p. 68°–70° C.

4-Ethylthio-2-trifluoromethylaniline is prepared utilizing the general method of Example 2 of U.S. Pat. No. 3,996,277.

EXAMPLE 3

N-Ethylsulfonyl-4-methylthio-2-trifluoromethylethanesulfonanilide

Ethanesulfonyl chloride (16.1 g., 0.125 mole) is added dropwise to a cold (0°–5° C.) stirred solution of 4-methylthio-2-trifluoromethylaniline (10.4 g., 0.05 mole) in pyridine (31.6 g., 0.4 mole). The solution is stirred at room temperature overnight, poured into ice water and 12 N hydrochloric acid (100 ml) with stirring to give N-ethylsulfonyl-4-methylthio-2-trifluoromethylethanesulfonanilide as an oil.

EXAMPLE 4

N-Methylsulfonyl-4-ethylthio-2-trifluoromethylmethanesulfonanilide

Methanesulfonyl chloride (11.5 g., 0.10 mole) is added dropwise to a cold (0°–5° C.) stirred solution of 4-ethylthio-2-trifluoromethylaniline (8.97 g., 0.04 mole) in pyridine (25.31 g., 0.32 mole). The solution is stirred at room temperature overnight, poured into ice water and 12 N hydrochloric acid (100 ml.) with stirring to give N-methylsulfonyl-4-ethylthio-2-trifluoromethylmethanesulfonanilide as a solid. A sample of this compound melts at 130°–135° C.

Additional compounds prepared using the same general method are as follows:
N-methylsulfonyl-4-n-propylthio-2-trifluoromethylmethanesulfonanilide, a solid
N-methylsulfonyl-4-tert-butylthio-2-trifluoromethylmethanesulfonanilide, m.p. 91°–93° C.
N-ethylsulfonyl-4-ethylthio-2-trifluoromethylethanesulfonanilide, a solid
N-ethylsulfonyl-4-isopropylthio-2-trifluoromethylethanesulfonanilide, an oil
N-n-propylsulfonyl-4-methylthio-2-trifluoromethylpropanesulfonanilide, an oil
N-n-butylsulfonyl-4-methylthio-2-trifluoromethylbutanesulfonanilide, an oil.

EXAMPLE 5

4-Methylthio-2-trifluoromethylethanesulfonanilide

A solution of N-ethylsulfonyl-4-methylthio-2-trifluoromethylethanesulfonanilide and 85 percent potassium hydroxide (10 g., 0.15 mole) in methanol (300 ml) is stirred for approximately 2.5 days at room temperature. The solvent is evaporated under reduced pressure, and the residue is taken up in hot water, filtered and then acidified with 12 N hydrochloric acid. The product is taken up in methylene chloride and dried. Removal of the drying agent and solvent gives an oil that crystallizes on treatment with hexane. Recrystallization from methylene chloride-hexane gives a golden solid, m.p. 52°–55° C.

| Analysis: | % C | % H | % N |
|---|---|---|---|
| Calculated for $C_{10}H_{12}F_3NO_2S_2$: | 40.1; | 4.0; | 4.7 |
| Found: | 39.9; | 4.0; | 4.6 |

EXAMPLE 6

4-Ethylthio-2-trifluoromethylmethanesulfonanilide.

A solution of N-methylsulfonyl-4-ethylthio-2-trifluoromethylmethanesulfonanilide (0.04 mole) and 85 percent potassium hydroxide (6.72 g., 0.12 mole) in methanol (300 ml.) is stirred for approximately 24 hours at room temperature. The solvent is evaporated under reduced pressure, and the residue is taken up in hot water, filtered and then acidified with 12 N hydrodchloric acid. The product is taken up in methylene chloride and the methylene chloride solution is washed with water. Removal of the solvent gives 4-ethylthio-2-trifluoromethyl methanesulfonanilide as an oil (11 g.). A purified sample melts at 50°–51° C.

Additional compounds prepared utilizing the same general method are as follows:
4-n-propylthio-2-trifluoromethylmethanesulfonanilide, b.p. 150°–156° C./5 mm
4-tert-butylthio-2-trifluoromethylmethanesulfonanilide, m.p. 98°–101° C.
4-ethylthio-2-trifluoromethylethanesulfonanilide, an oil
4-isopropylthio-2-trifluoromethylethanesulfonanilide, m.p. 51°–53° C.
4-methylthio-2-trifluoromethylpropanesulfonanilide, m.p. 67°–70° C.
4-methylthio-2-trifluoromethylbutanesulfonanilide, m.p. 46°–55° C.
4-tert-butylthio-2-trifluoromethylethanesulfonanilide, m.p. 67°–69° C.

The following is an alternative process for the preparation of 4-ethylthio-2-trifluoromethylmethanesulfonanilide:

Methanesulfonyl chloride (8.6 g, 0.075 mole) is added dropwise to a cold (0°–5° C.) stirred solution of 4-ethylthio-2-trifluoromethylaniline (11.64 g., 0.05 mole) in pyridine (15.82 g, 0.20 mole). The solution is stirred at room temperature overnight. Thin layer chromatography on silica gel with methylene chloride eluant alongside authentic samples indicates formation of a mixture consisting of about two-thirds 4-ethylthio-2-trifluoromethylmethanesulfonanilide and one-third N-methylsulfonyl-4-ethylthio-2-trifluoromethylmethanesulfonanilide. The reaction mixture is then heated at reflux for six hours, cooled and poured into dilute hydrochloric acid. The resulting solid is washed with water three times and dried to give 14 g of 4-ethylthio-2-trifluoromethylmethanesulfonanilide.

In a similar way, but using 3-bromopyridine in place of pyridine, 4-methylthio-2-trifluoromethylisopropanesulfonanilide is prepared as an oil.

| Analysis: | % C | % H | % N |
|---|---|---|---|
| Calculated for $C_{11}H_{14}F_3NO_2S_2$: | 42.2 | 4.5 | 4.5 |
| Found: | 42.6 | 4.4 | 4.5 |

EXAMPLE 7

4-Methylsulfinyl-2-trifluoromethylethanesulfonanilide

To a stirred solution of 4-methylthio-2-trifluoromethylethanesulfonanilide (3 g., 0.01 mole) in glacial acetic acid (25 ml) is added 30 percent hydrogen peroxide (1.13 g., 0.01 mole). The solution is stirred overnight at room temperature, heated just to reflux then treated with water. The aqueous mixture is extracted with methylene chloride, washed with water and dried. Removal of the drying agent and solvent gives a yellow oil. Crystallization from methylene chloride-hexane produces a white solid, m.p. 82°–85° C.

| Analysis: | % C | % H | % N |
|---|---|---|---|
| Calculated for $C_{10}H_{12}F_3NO_2S_2$: | 38.0; | 3.8; | 4.4 |
| Found: | 38.0; | 3.8; | 4.4. |

The following compounds are prepared utilizing the same general method:
4-ethylsulfinyl-2-trifluoromethylmethanesulfonanilide, an oil
4-tert-butylsulfinyl-2-trifluoromethylethanesulfonanilide, m.p. 133°–135° C.
4-ethylsulfinyl-2-trifluoromethylethanesulfonanilide, yellow paste.
4-isopropylsulfinyl-2-trifluoromethylmethanesulfonanilide, an oil.

EXAMPLE 8

An increased scale preparation of 4-ethylsulfinyl-2-trifluoromethylmethanesulfonanilide To a cold (10° C.) stirred solution of 4-ethylthio-2-trifluoromethylmethanesulfonanilide (8520 g) in glacial acetic acid (17,032 ml) is added 30 percent hydrogen peroxide (3,230 g). The solution is stirred and allowed to warm to room temperature. An additional 392 g of 30 percent hydrogen peroxide is added and the reaction mixture stirred for two hours. Water (34,065 ml) is added and the reaction mixture filtered through filter aid. The filtrate is extracted with methylene chloride, the combined methylene chloride extracts are washed with water and dried (magnesium sulfate). Removal of the drying agent and solvent gives an oil (7,045 g) which solidifies on standing to an oily solid, m.p. 87°–101° C.

| Analysis: | % C | % H | % N |
|---|---|---|---|
| Calculated for $C_{10}H_{12}F_3NO_3S_2$: | 38.1 | 3.8 | 4.4 |
| Found: | 38.4 | 3.8 | 4.6 |

EXAMPLE 9

4-Methylsulfonyl-2-trifluoromethylethanesulfonanilide

To a stirred solution of 4-methylthio-2-trifluoromethylethanesulfonanilide (1.5 g., 0.005 mole) in glacial acetic acid (15 ml) is added 30 percent hydrogen peroxide (2.3 g., 0.02 mole). The solution is heated at reflux for 2.5 hours, water is added, and the mixture is cooled.

The resulting precipitate is collected by filtration, washed with water and dried to give a white solid, m.p. 156°–159° C.

| Analysis: | % C | % H | % N |
|---|---|---|---|
| Calculated for $C_{10}H_{12}F_3NO_4S_2$: | 36.2; | 3.6; | 4.2 |
| Found: | 36.2; | 3.6; | 4.1. |

Additional compounds prepared utilizing the same general method are as follows:
4-ethylsulfonyl-2-trifluoromethylmethanesulfonanilide, m.p. 141°–144° C.
4-propylsulfonyl-2-trifluoromethylmethanesulfonanilide, m.p. 155°–158° C.
4-tert-butylsulfonyl-2-trifluoromethylethanesulfonanilide, m.p. 143°–147° C.
4-isopropylsulfonyl-2-trifluoromethylmethanesulfonanilide, m.p. 134°–143° C.
4-tert-butylsulfonyl-2-trifluoromethylmethanesulfonanilide, m.p. 195°–200° C.
4-ethylsulfonyl-2-trifluoromethylethanesulfonanilide, m.p. 82°–86° C.
4-methylsulfonyl-2-trifluoromethylpropanesulfonanilide, m.p. 152°–157° C.
4-methylsulfonyl-2-trifluoromethylbutanesulfonanilide, m.p. 93°–113° C.
4-methylsulfonyl-2-trifluoromethylisopropanesulfonanilide, m.p. 110°–112° C.

EXAMPLE 10

An increased scale preparation of 4-ethylsulfonyl-2-trifluoromethylmethanesulfonanilide To a stirred solution of 4-ethylthio-2-trifluoromethylmethanesulfonanilide (2270 g.) in glacial acetic acid (3500 ml) is added 30 percent hydrogen peroxide (2584 g). The solution is heated at reflux for 1 hour, water is added, and the mixture is cooled. The resulting precipitate is collected by filtration, washed with water and dried to give a white solid, m.p. 146°–148° C.

| Analysis: | % C | % H | % N |
|---|---|---|---|
| Calculated for $C_{10}H_{12}F_3NO_4S_2$: | 36.2; | 3.6; | 4.2 |
| Found: | 35.3; | 3.6; | 4.2 |

EXAMPLE 11

4-Thiocyano-2-trifluoromethylaniline

To a cold (0°–5° C.) stirred solution of 2-aminobenzotrifluoride (6.44 g., 0.04 mole) and sodium thiocyanate (9.72 g., 0.12 mole) in methanol (100 ml) is added dropwise a solution of bromine (6.6 g., 0.42 mole) in methanol (25 ml) saturated with sodium bromide. The solution is stirred for 20 minutes following the addition of bromine and then poured into water (750 ml) and neutralized with sodium carbonate. The resulting oil is taken up in methylene chloride and dried. Removal of the drying agent and solvent gives 4-thiocyano-2-trifluoromethylaniline as an oil that solidifies on standing (8.4 g., 96 percent yield). A purified sample has a melting point of 52°–55° C. and the following analysis:

| Analysis: | % C | % H | % N |
|---|---|---|---|
| Calculated for $C_8H_5F_3N_2S$: | 44.0; | 2.3 | 12.8 |
| Found: | 43.7; | 2.3; | 12.9. |

EXAMPLE 12

4-Methylthio-2-trifluoromethylaniline

A solution of 4-thiocyano-2-trifluoromethylaniline (1.09 g., 0.005 mole) and sodium cyanide (0.125 g., 0.0025 mole) in methanol (50 ml) is refluxed for about 16 hours. Methanol is removed from the cool reaction mixture by evaporation under reduced pressure, the residue is taken up in methylene chloride, washed with water and dried. Removal of the drying agent and solvent gives the product as a yellow oil (1 g., 91 percent yield).

The following additional compounds are prepared utilizing the same general method:
4-isopropylthio-2-trifluoromethylaniline, an oil
4-n-propylthio-2-trifluoromethylaniline, an oil.

EXAMPLE 13

4-Methylthio-2-trifluoromethylaniline prepared using an alternate procedure

A solution of 4-thiocyano-2-trifluoromethylaniline (2.1 g., 0.01 mole) in ethanol (25 ml) is added to a stirred solution of sodium sulfide nonahydrate (2.4 g., 0.01 mole) in water (5 ml) and the mixture is warmed (50° C.) for 40 minutes. Methyl iodide (1.55 g., 0.011 mole) is added to the warm reaction all at once, and stirring is continued for two hours. Thin layer chromatography on silica gel with 50 percent hexane-50 percent methylene chloride diluent alongside an authentic sample shows that all of the thiocyano compound is reacted to produce the desired product.

EXAMPLE 14

4-Bromo-2-trifluoromethylmethanesulfonanilide

To a stirred solution of 2-trifluoromethylmethanesulfonanilide (prepared from 2-aminobenzotrifluoride utilizing procedures analogous to those of Examples 3 and 4 hereof) in water-ethanol (40 ml-150 ml) solvent mixture is added bromine (6.7 g., 0.042 mole) dropwise. The reaction mixture is then heated to reflux and refluxing is continued for two hours. The reaction mixture is cooled and placed under vacuum to remove most of the solvent. The oil which remains is taken up in methylene chloride (100 ml), and residual water is removed with a separatory funnel, and the methylene chloride solution is dried. Removal of the drying agent and methylene chloride gives an oil that solidifies on treatment with hexane. The solid is recrystallized from hexane-methylene chloride, m.p. 62°–66° C.

| Analysis: | % C | % H | % N |
|---|---|---|---|
| Calculated for $C_8H_7BrF_3NO_2S$: | 30.2; | 2.2; | 4.4 |
| Found: | 30.5; | 2.2; | 4.4. |

EXAMPLE 15

4-Isopropylthio-2-trifluoromethylmethanesulfonanilide

Cuprous thioisopropoxide is prepared by stirring a mixture of isopropyl mercaptan (15.2 g., 0.2 mole), cuprous oxide (14.3 g., 0.1 mole) and ethanol (250 ml) at reflux overnight. Removal of the solvent by evaporation and washing the residual solid with ethanol gives 26.6 g. of product.

A mixture of cuprous thioisopropoxide (3.1 g., 0.022 mole), 4-bromo-2-trifluoromethylmethanesulfonanilide (6.3 g., 0.0198 mole), pyridine (30 ml) and quinoline (30 ml) is heated at 190° C. for two hours after solution is achieved. The reaction solution is then cooled to 100° C. and poured into a 12 N hydrochloric acid-wet ice mixture, and the mixture is extracted with chloroform. The chloroform is evaporated, and the residual oil is heated for two hours with 5 percent sodium hydroxide (300 ml). The basic medium is clarified by treatment with charcoal, washed with methylene chloride, and then acidified to give an oil. The oil is extracted with methylene chloride, the combined extracts are dried and stripped to give 4.5 g. of product. Distillation gives 2.3 g. (b.p. 130°–150° C./5 mm. Hg) of a product which is further purified by recrystallization from hexane-methylene chloride. The resulting product, 4-isopropylthio-2-trifluoromethylmethanesulfonanilide, has a melting point of 56°–60° C.

| Analysis: | % C | % H | % N |
|---|---|---|---|
| Calculated for $C_{11}H_{14}F_3NO_2S_2$: | 42.2; | 4.5; | 4.5 |
| Found: | 41.6; | 4.4; | 4.4. |

4-n-Propylthio-2-trifluoromethylmethanesulfonanilide, b.p. 150°–156° C./5 mm Hg, is also prepared utilizing the same general method.

EXAMPLE 16

4-Ethylthio-2-trifluoromethylmethanesulfonanilide

N-Methylsulfonyl-4-thiocyano-2-trifluoromethylmethanesulfonanilide (4.5 g., 0.012 mole), prepared from 4-thiocyano-2-trifluoromethylaniline (of Example 11) utilizing a procedure analogous to that of Example 3 hereof, is added to a solution of 85 percent potassium hydroxide (2.4 g., 0.036 mole) in ethanol (100 ml). This solution is stirred at room temperature overnight, the ethanol is then evaporated and the residue heated with water. The aqueous mixture is filtered, and the filtrate is acidified to give an oil. Extraction of the oil with methylene chloride, drying, washing with water and removal of the methylene chloride gives the desired product as an oil.

4-Isopropylthio-2-trifluoromethylmethanesulfonanilide is also prepared utilizing this procedure.

PLANT GROWTH REGULATING AND HERBICIDAL INFORMATION

Information is presented in Examples 17–20 relative to the biological activity of a number of compounds of the invention and prior art compounds. Each of the compounds is designated in these examples by a three digit number which specifies its structure. Thus, referring to formula I at the beginning of the specification, the first digit indicates the number of carbon atoms in $R^1$, the second digit indicates the number of carbon atoms in $R^2$ and the third digit indicates the value of n. The prior art compounds appear first followed by the compounds of the invention which differ the least structurally from the art compounds (120–122 and 210–212) and then by other compounds of the invention. The compounds are as follows:

110. 4-Methylthio-2-trifluoromethylmethanesulfonanilide (the compound of Example 4 of U.S. Pat. No. 3,996,277)
112. 4-Methylsulfonyl-2-trifluoromethylmethanesulfonanilide (the compound of Example 6 of U.S. Pat. No. 3,996,277)
120. 4-Ethylthio-2-trifluoromethylmethanesulfonanilide (the compound of Example 6)
121. 4-Ethylsulfinyl-2-trifluoromethylmethanesulfonanilide (the compound of the first preparation following Example 7 and of Example 8)
122. 4-Ethylsulfonyl-2-trifluoromethylmethanesulfonanilide (the compound of the first preparation following Example 9 and of Example 10)
210. 4-Methylthio-2-trifluoromethylethanesulfonanilide (the compound of Example 5)
211. 4-Methylsulfinyl-2-trifluoromethylethanesulfonanilide (the compound of Example 7)
212. 4-Methylsulfonyl-2-trifluoromethylethanesulfonanilide (the compound of Example 9)
220. 4-Ethylthio-2-trifluoromethylethanesulfonanilide (the third preparation following Example 6)
222. 4-Ethylsulfonyl-2-trifluoromethylethanesulfonanilide (the sixth preparation following Example 9)
130. 4-Isopropylthio-2-trifluoromethylmethanesulfonanilide (the compound of Example 15)
132. 4-Isopropylsulfonyl-2-trifluoromethylmethanesulfonanilide (the fourth preparation following Example 9)
140. 4-Tert-butylthio-2-trifluoromethylmethanesulfonanilide (the second preparation following Example 6)
142. 4-Tert-butylsulfonyl-2-trifluoromethylmethanesulfonanilide (the fifth preparation following Example 9)
230. 4-Isopropylthio-2-trifluoromethylethanesulfonanilide (the fourth preparation following Example 6)
240. 4-Tert-butylthio-2-trifluoromethylethanesulfonanilide (the seventh preparation following Example 6)
242. 4-Tert-butylsulfonyl-2-trifluoromethylethanesulfonanilide (the third preparation following Example 9)

EXAMPLE 17

Herbicidal Activity—Selective Control of Rhizomatous Johnsongrass in the Presence of Cotton, Corn and Soybeans The following preemergence greenhouse tests demonstrate that certain compounds of the present invention control established rhizomatous johnsongrass (*Sorghum halepense* (*L. Pers.*)) at rates of application tolerated by cotton, corn and soybeans. A previously known compound of similar chemical structure performs similarly with respect to cotton, but not with respect to corn and soybeans.

The tests were carried out as follows:

Plastic flats 12×20×2 inches were used for the tests. Each was filled with pasteurized soil to ¾ inch from the top. A generous handful of johnsongrass rhizomes was buried throughout the area of the flat. The soil was packed, and thirty seeds each of corn, cotton and soybeans were placed in three rows of ten. An additional one quarter inch of soil was added, covering all of the seeds.

The flats were immediately sprayed with dilute formulations of the indicated compounds at given rates (calculated in pounds of the compound per acre). Rates applied were 2, 1, 0.5 and 0.25 pounds per acre. Three replications of each rate and compound were used. The containers were placed in a greenhouse and were watered as needed.

Six weeks after treatment they were rated for growth inhibition and phytotoxicity relative to untreated control containers. The rating scheme and the results obtained are as follows:

GROWTH INHIBITION RATING

A—Equal to control
B—Slight to ¼ growth inhibition
C—Moderate ¼ to ½ growth inhibition
D—½ to ¾ growth inhibition
E—¾ to complete growth inhibition

PHYTOTOXICITY RATING

1—No injury or normal stand
2—Slight injury or slight stand reduction
3—Moderate injury or moderate stand reduction
4—Severe injury or severe stand reduction
5—All plants killed or no stand

| Compound | Application Rate (lb) per acre | Growth Inhibition and Phytotoxicity Ratings | | | |
|---|---|---|---|---|---|
| | | Rhizomatous Johnsongrass | Cotton | Corn | Soybeans |
| 112 | 2. | E 4 | A 1 | E 5 | E 4 |
| | 1. | E 4 | A 1 | E 5 | E 4 |
| | .5 | E 4 | A 1 | E 4 | E 4 |
| | .25 | D 4 | A 1 | E 4 | D 4 |
| 211 | 2. | E 3 | A 1 | D 4 | E 4 |
| | 1. | E 3 | A 1 | A 2 | E 4 |
| | .5 | D 2 | A 1 | A 1 | E 4 |
| | .25 | D 2 | A 1 | A 1 | E 4 |
| 130 | 2. | E 2 | A 1 | E 5 | B 2 |
| | 1. | D 3 | A 1 | E 4 | A 2 |
| | .5 | C 2 | A 1 | E 4 | A 2 |
| | .25 | C 2 | A 1 | E 4 | A 2 |
| 132 | 2. | D 2 | A 1 | D 4 | B 2 |
| | 1. | D 2 | A 1 | D 4 | A 2 |
| | .5 | B 1 | A 1 | C 3 | A 1 |
| | .25 | A 1 | A 1 | C 2 | A 1 |

EXAMPLE 18

Herbicidal Activity—Selective Control in a Variety of Crop—Weed Combinations

An effective selective herbicide in a given weed-crop combination is one which will control or eradicate the weed at a rate of application at which it is tolerated by the crop (i.e., the crop is substantially unaffected).

The following weed and crop species were planted in rectangular plastic flats containing pasturized sandy loam soil.

| Grasses | Weeds Rhizomes | Sedge | Crops |
|---|---|---|---|
| Goosegrass | Johnsongrass | Nutsedge | Cotton |
| Wild Oats | | | Corn |
| Cheatgrass | | | Soybeans |
| Barnyardgrass | | | Wheat |
| | | | Rice |
| | | | Sorghum |
| | | | Sugar Beets |

The flats were immediately sprayed with dilute formulations of the indicated compounds at given rates (calculated in pounds of the compound per acre). Rates applied were 2, 1, 0.5, 0.25 and 0.125 pounds per acre. Two replications of each rate and compound were used. The containers were placed in a greenhouse and were watered as needed.

Four weeks after treatment they were rated relative to untreated control containers. The rating scheme and the results obtained are as follows:

HERBICIDAL RATING RELATING TO WEEDS

E=Excellent, 90–100% kill
G=Good, 70–90% kill
F=Fair, 60–70% kill
P=Poor, less than 60% kill

TOLERANCE OR SUSCEPTIBILITY OF THE CROPS TO THE TREATMENTS

S=Susceptible—Exhibits injury, stand reduction or phytotoxic growth.
T=Tolerant—No discernible difference from untreated control.

| Cpd | Rate (lb/acre) | Goosegrass | Wild Oats | Cheatgrass | Barnyardgrass | Johnsongrass | Nutsedge | Cotton | Corn | Soybean | Wheat | Rice | Sorghum | Sugar Beets |
|---|---|---|---|---|---|---|---|---|---|---|---|---|---|---|
| 110 | 2. | P | E | P | E | E | G | T | S | S | S | S | S | T |
| | 1. | P | G | P | E | E | P | T | S | S | S | S | S | T |
| | 0.5 | P | P | P | P | G | P | T | S | S | S | S | S | T |
| | 0.25 | P | P | P | P | F | P | T | S | S | T | S | T | T |
| | 0.125 | P | P | P | P | P | P | T | T | S | T | T | T | T |
| 120 | 2. | E | E | E | E | E | E | T | S | S | S | S | S | T |
| | 1. | P | E | E | E | E | G | T | S | S | S | S | S | T |
| | 0.5 | P | E | E | E | E | P | T | S | S | S | S | S | T |
| | 0.25 | P | E | G | G | G | P | T | S | S | S | S | S | T |
| | 0.125 | P | G | G | P | F | P | T | S | S | T | T | S | T |
| 210 | 2. | P | E | E | E | E | E | T | S | S | S | S | S | T |
| | 1. | P | E | E | E | E | E | T | T | S | S | S | S | T |
| | 0.5 | P | E | E | E | E | P | T | T | S | S | S | S | T |
| | 0.25 | P | E | P | P | E | P | T | T | S | S | S | S | T |
| | 0.125 | P | P | P | P | E | P | T | T | S | T | S | T | T |
| 220 | 2. | P | E | E | E | E | G | T | S | S | S | S | S | T |
| | 1. | P | E | E | E | G | G | T | S | S | S | S | S | T |
| | 0.5 | P | E | E | E | G | P | T | T | S | S | S | S | T |
| | 0.25 | P | E | E | E | G | P | T | S | S | S | S | S | T |
| | 0.125 | P | E | G | P | G | P | T | T | T | S | S | S | T |
| 130 | 2. | E | E | E | E | G | E | T | S | T | S | S | S | T |
| | 1. | E | E | E | E | G | F | G | T | S | T | S | S | S | T |

-continued

| Cpd | Rate (lb/acre) | Goose-grass | Wild Oats | Cheat-grass | Barn-yard-grass | Johnson-grass | Nut-sedge | Cotton | Corn | Soy-bean | Wheat | Rice | Sorghum | Sugar Beets |
|---|---|---|---|---|---|---|---|---|---|---|---|---|---|---|
| | 0.5 | P | G | G | P | P | P | T | S | T | S | S | S | T |
| | 0.25 | P | P | P | P | P | P | T | S | T | S | S | T | T |
| | 0.125 | P | P | P | P | P | P | T | T | T | S | T | T | T |
| 140 | 2. | P | P | P | G | P | P | T | T | T | S | S | S | T |
| | 1. | P | P | P | G | P | P | T | T | T | S | S | S | T |
| | 0.5 | P | P | P | P | P | P | T | T | T | S | S | S | T |
| | 0.25 | P | P | P | P | P | P | T | T | T | T | S | S | T |
| | 0.125 | P | P | P | P | P | P | T | T | T | T | S | T | |
| 240 | 2. | P | P | E | P | P | P | T | T | T | S | S | S | S |
| | 1. | P | P | E | P | P | P | T | T | T | T | T | T | T |
| | 0.5 | P | P | P | P | P | P | T | T | T | T | T | T | T |
| | 0.25 | P | P | P | P | P | P | T | T | T | T | T | T | T |
| | 0.125 | P | P | P | P | P | P | T | T | T | T | T | T | T |

EXAMPLE 19

Plant Growth Regulation—Tobacco Sucker Control

Tobacco growers normally top growing tobacco plants sometime (e.g., 2–4 weeks) before harvest in order to remove the main terminal bud, thereby increasing lateral growth and leaf size. However, undesirable regrowth also occurs following topping, several buds competing to become the new main terminal bud in each. Such regrowths, which are referred to as tobacco suckers, result in substantial reductions in over all tobacco leaf yields and consequently in major economic losses throughout the industry.

Extensive research work has been carried out in the area of tobacco sucker suppression by the U.S. Department of Agricultural and others to identify chemical treatments which will reduce or prevent the sucker growth until harvest with little or no damage to the plant (phytotoxicity).

The following greenhouse tests demonstrate that certain of the compounds of the present invention are active tobacco suppression agents, i.e., they effectively suppress tobacco sucker growth until after the normal harvest time (approximately one month after treatment) whereas a previously known compound of similar chemical structure does not have this property.

Xanthii variety tobacco plants are transplanted to 6-inch pots when the plants are 2–3 inches in height. When they have grown to the button stage (i.e., the pre-bloom stage at which the flower first appears), the upper fourth of the plant is severed from the lower three-fourths of the plant. The plants are then sprayed with dilute (1000 ppm and 500 ppm) solutions of the compounds in acetone and placed in the greenhouse. Two replications of the 1000 ppm test and three replications of the 500 ppm test of each compound are used.

The plants are rated for sucker growth inhibition and phytotoxicity (injury to the entire plant) relative to untreated controls according to the following scheme:

SUCKER GROWTH INHIBITION RATING

A—Equal to control
B—Slight to ¼ growth inhibition
C—Moderate ¼ to ½ growth inhibition
D—½ to ¾ growth inhibition
E—¾ to complete growth inhibition

PHYTOTOXICITY RATING

1—No injury or normal stand
2—Slight injury or slight stand reduction
3—Moderate injury or moderate stand reduction
4—Severe injury or severe stand reduction
5—All plants killed or no stand The results are set forth in the following table:

| Cpd | Application Rate (ppm) | Sucker Growth Inhibition & Phytotoxicity Rating - Days After Application | | | |
|---|---|---|---|---|---|
| | | 10 | 20 | 40 | 60 |
| 112 | 1000 | A1 | A1 | A1 | A1 |
| | 500 | A1 | A1 | A1 | A1 |
| 120 | 1000 | D1 | B1 | C1 | A1 |
| | 500 | D1 | B1 | B1 | A1 |
| 122 | 1000 | D1 | D1 | D1 | A1 |
| | 500 | A1 | A1 | A1 | A1 |
| 210 | 1000 | E1 | E1 | D1 | A1 |
| | 500 | E1 | C1 | D1 | A1 |
| 211 | 1000 | D1 | C1 | C1 | B1 |
| | 500 | E1 | B1 | C1 | A1 |
| 212 | 1000 | E1 | B1 | C1 | A1 |
| | 500 | C1 | A1 | A1 | A1 |
| 220 | 1000 | E1 | E1 | C1 | A1 |
| | 500 | D1 | D1 | B1 | A1 |
| 222 | 1000 | E1 | B1 | B1 | A1 |
| | 500 | D1 | A1 | B1 | A1 |
| 130 | 1000 | A1 | A1 | A1 | A1 |
| | 500 | A1 | A1 | A1 | A1 |
| 132 | 1000 | A1 | A1 | A1 | A1 |
| | 500 | A1 | A1 | A1 | A1 |
| 142 | 1000 | B1 | A1 | A1 | A1 |
| | 500 | A1 | A1 | A1 | A1 |
| 230 | 1000 | A1 | A1 | A1 | A1 |
| | 500 | A1 | A1 | A1 | A1 |
| 242 | 1000 | D1 | C1 | C1 | A1 |
| | 500 | A1 | A1 | A1 | A1 |

EXAMPLE 20

Plant Growth Regulation—Citrus (Orange) Acidity Reduction

The proper balance of sweetness and acidity (tartness) is of critical importance to the flavor of citrus fruit products. In fact, the ratio of these two factors (suitably measured) serves as an index of flavor. Test procedures for the determination of the sweetness (often referred to as "BRIX sweetness" or simply as "BRIX") and acid determinations are described in the articles "The Flordia Department of Citrus Cooperative Chemical Screening Programs for Citrus," Proc. Int. Soc. Citriculture 1977, Vol. 2, pps. 692–696 and in the literature cited therein. Generally, BRIX/acid ratios of about 13 are desired before harvesting oranges for processing into juice. A ten percent (10%) increase in the BRIX/acid ratio (compared with the control) is considered to be an important advantage and increases somewhat below ten percent are significant. Both the year (the growing season) and the variety of orange affect the BRIX and acid readings and therefore only tests run during the same year and utilizing the same variety of orange can be meaningfully compared.

Acceptable sweetness for the processed fruit cannot be developed by simply adding sugar or sweetening sources from other fruits without destroying the essential flavor of the product. Thus, under Florida law, if the product is to be sold as "orange juice", no sugar (or other additive) can be utilized. The fruit normally increases in sweetness as it ripens further on the trees and higher sweetness to acidity ratios can therefore be expected from later harvests. However, this is economically disadvantageous and may still not result in the desired ratio. Blending lots of fruit may also help and in practice, large quantities of Florida orange juice destined for use in frozen concentrated orange juice are blended with orange juice from other orange growing states to obtain the proper balance of sweetness to acidity.

A potentially more attractive solution to the problem is the application of a growth regulator to the citrus trees prior to harvest to increase the sweetness to acidity ratio. Lead arsenate has been found to have this effect and has been used in the past. However, it has certain disadvantages which make its future use unlikely. These include environmental and safety concerns and an excessive lowering of acidity which accompanies its use (resulting in an unacceptably flat taste). It is in fact now illegal to use lead arsenate on oranges in Florida (although it can still be used on grapefruit) and by the end of 1980 it will be illegal to utilize it on any citrus in California. The United States Environmental Protection Agency has furthermore issued a REBUTTABLE PRESUMPTION AGAINST REGISTRATION (RPAR) order relative to its use. For these reasons it is important to find a suitable alternative growth regulator for increasing the sweetness to acidity ratio of citrus fruit.

An extensive screening program has been carried out by the citrus industry to identify compounds which would have the effect of increasing the sweetness and decreasing the acidity of oranges. However, few positive leads have been found. The principal screening test utilized in this program is an orange tree branch test which is described in the article in the Proc. Int. Soc. Citriculture article cited above. This test requires one liter of test solution and at least twenty (20) fruit are evaluated per lot. Three replications are used per test chemical, all applied to the same tree. Sprays are normally applied to the immature fruit in June, test samples are harvested about December 1st and a control sample is taken from each treated tree at the time of harvest (the control samples are pooled for all trees sprayed on a particular day). The BRIX sweetness and acidity are determined for each lot. The results from this branch test have been found to correlate well with the actual observation from whole tree treatments.

The following results have been obtained utilizing the orange tree branch test to evaluate compounds of the present invention compared with the prior art compounds 110 and 112.

| Orange Variety/ Year Tested | Cpd | Application Rate (ppm) | Brix/ Acid Ratio | Percent Deviation from Untreated Control |
|---|---|---|---|---|
| Hamlin/1977 | 110 | 1000 | 10.67 | −9.6 |
| " | 112 | 1000 | 10.63 | −9.9 |
| " | Control | 0 | 11.80 | 0 |
| Hamlin/1978 | 120 | 1000 | 20.00 | 14.4 |
| " | 122 | 1000 | 20.29 | 16.1 |
| " | 211 | 1000 | 16.01 | −8.4 |
| " | 212 | 1000 | 17.56 | 0.5 |
| " | 220 | 1000 | 18.46 | 5.6 |
| " | 222 | 1000 | 16.75 | −4.2 |
| " | 130 | 1000 | 15.98 | −8.6 |
| " | 132 | 1000 | 17.55 | 0.4 |
| " | Control | 0 | 17.48 | 0 |
| Hamlin/1978 Test 2 | 220 | 1000 | 19.10 | 8.9 |
| Hamlin/1978 Test 2 | 222 | 1000 | 18.09 | 3.1 |
| | Control | 0 | 17.54 | 0 |

Follow up whole tree tests have also been carried out to further evaluate compounds of the invention. In this test procedure, two whole trees (two replicates) are sprayed for each concentration and compound. As in the initial screen test, the sprays are applied to the immature fruit in June and the test samples (40 fruit per tree) are harvested about December first. Control samples are taken from three trees in the general vicinity of the test trees (40 fruit from each control tree) and the control samples are pooled. The results obtained are as follows:

| Orange Variety/ Year Tested | Cpd | Application Rate (ppm) | Brix/ Acid Ratio | Percent Deviation from Untreated Control |
|---|---|---|---|---|
| Valencia | 120 | 1000 | 9.13 | 9.5 |
| " | 121 | 1000 | 9.08 | 8.9 |
| " | 122 | 1500 | 9.25 | 10.9 |
| " | Control | 0 | 8.34 | 0 |
| Hamlin/1979 | 120 | 1000 | 14.85 | 16.8 |
| " | 121 | 1000 | 14.98 | 17.9 |
| " | 122 | 1000 | 15.04 | 18.3 |
| " | Control | 0 | 12.71 | 0 |

The following are shown by the data of Examples 17–20:

Compound 120 is active as a selective herbicide to control cheatgrass in cotton, sugar beets, wheat and rice as well as wild oats in wheat and rice and as a plant growth regulator to increase the sweetness to acidity ratio of oranges, whereas the prior art compound 110 does not share those activities.

In addition, compound 120 is active as a selective herbicide to control wild oats, barnyardgrass, johnsongrass and nutsedge in cotton and sugar beets and as a plant growth regulator to control tobacco sucker growth.

Compound 121 is active as a plant growth regulator to increase the sweetness to acidity ratio in oranges.

Compound 122 is active as a plant growth regulator to increase the sweetness to acidity ratio of oranges whereas the prior art compound 112 does not share that activity.

In addition, compound 122 controls tobacco sucker growth at an application rate of 1000 ppm whereas compound 112 is totally inactive at the application rates tested.

Compound 210 is active as a herbicide to control cheatgrass in cotton, corn and sugar beets; and wild oats, barnyardgrass, johnsongrass and nutsedge in corn; and johnsongrass in rice, whereas the prior art compound 110 does not share those activities.

In addition, compound 210 is active as a selective herbicide to control wild oats, barnyardgrass, johnsongrass and nutsedge in cotton and sugar beets and as a plant growth regulator to control tobacco sucker growth.

Compound 211 is active as a selective herbicide to control johnsongrass in corn and as a plant growth regulator to control tobacco sucker growth.

Compound 212 is active as a plant growth regulator to control tobacco sucker growth at an application rate of 1000 ppm whereas the prior art compound 112 is totally inactive at that application rate.

Compound 220 is active as a selective herbicide to control cheatgrass in cotton and sugar beets; wild oats, cheatgrass and barnyardgrass and johnsongrass in corn; and wild oats, cheatgrass and johnsongrass in soybeans; and as a plant growth regulator to increase the sweetness to acidity ratio of oranges whereas the prior art compound 110 does not share those activities.

In addition, compound 220 is active as a selective herbicide against wild oats, barnyardgrass, johnsongrass and nutsedge in cotton and sugar beets and as a plant growth regulator to control tobacco sucker growth at application rates of 500 and 1000 ppm.

Compound 222 is active as a plant growth regulator to control tobacco sucker growth at application rates of 500 and 1000 ppm whereas the prior art compound 112 does not share that activity.

Compound 130 is active as a selective herbicide to control goosegrass and cheatgrass in cotton, soybeans and sugar beets; and wild oats, barnyardgrass, johnsongrass and nutsedge in soybeans whereas the prior art compound 110 does not share those activities.

In addition, compound 130 is active as a selective herbicide to control wild oats, barnyardgrass, johnsongrass and nutsedge in cotton and sugar beets.

Compounds 132 is active as a selective herbicide to control johnsongrass in soybeans whereas the prior art compound 112 does not share that activity.

In addition, compound 132 is active to control johnsongrass in cotton.

Compound 140 is active as a selective herbicide to control barnyardgrass in corn and soybeans whereas compound 110 does not share those activities.

In addition, compound 140 is active to control barnyardgrass in cotton and sugar beets.

Compound 142 has activity as a plant growth regulator to control tobacco sucker growth at 1000 ppm and at the interval of ten days after application.

Compound 240 is active as a selective herbicide to control cheatgrass in cotton, corn, soybeans, wheat, rice, sorghum and sugar beets whereas the prior art compound 110 does not share those activities.

Compound 242 is active as a plant growth regulator to control tobacco sucker growth at an application rate of 1000 ppm whereas the prior art compound 112 does not share that activity.

What is claimed is:
1. A compound of the formula

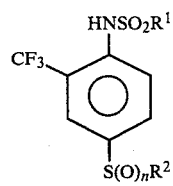

wherein $R^1$ and $R^2$ are independently alkyl groups containing from 1 to 4 carbon atoms and n is 0–2, provided that $R^1$ and $R^2$ are not both methyl, and agriculturally acceptable salts thereof.

2. A compound according to claim 1 wherein n is zero.
3. A compound according to claim 1 wherein n is 1.
4. A compound according to claim 1 wherein n is 2.
5. A compound according to claim 1 wherein $R^1$ and $R^2$ are selected from methyl and ethyl.
6. A compound according to claim 5 wherein $R^1$ is methyl and $R^2$ is ethyl.
7. A compound according to claim 5 wherein $R^1$ is ethyl and $R^2$ is methyl.
8. A compound according to claim 5 wherein $R^1$ is ethyl and $R^2$ is ethyl.
9. A compound according to claim 2 wherein $R^1$ and $R^2$ are selected from methyl and ethyl.
10. The compound 4-ethylthio-2-trifluoromethylmethanesulfonanilide according to claim 9.
11. The compound 4-methylthio-2-trifluoromethylethanesulfonanilide according to claim 9.
12. The compound 4-ethylthio-2-trifluoromethylethanesulfonanilide according to claim 9.
13. A compound according to claim 3 wherein $R^1$ and $R^2$ are selected from methyl and ethyl.
14. The compound 4-ethylsulfinyl-2-trifluoromethylmethanesulfonanilide according to claim 13.
15. The compound 4-methylsulfinyl-2-trifluoromethylethanesulfonanilide according to claim 13.
16. A compound according to claim 4 wherein $R^1$ and $R^2$ are selected from methyl and ethyl.
17. The compound 4-ethylsulfonyl-2-trifluoromethylmethanesulfonanilide according to claim 16.
18. The compound 4-methylsulfonyl-2-trifluoromethylethanesulfonanilide according to claim 16.
19. The compound 4-ethylsulfonyl-2-trifluoromethylethanesulfonanilide according to claim 16.
20. A compound according to claim 1 wherein $R^2$ is isopropyl.
21. The compound 4-isopropylthio-2-trifluoromethylmethanesulfonanilide according to claim 20.
22. The compound 4-isopropylsulfonyl-2-trifluoromethylmethaneulfonanilide according to claim 20.
23. A compound according to claim 1 wherein $R^2$ is tert-butyl.
24. The compound 4-tert-butylthio-2-trifluoromethylmethanesulfonanilide according to claim 23.
25. The compound 4-tert-butylthio-2-trifluoromethylethanesulfonanilide according to claim 23.
26. The compound 4-tert-butylsulfonyl-2-trifluoromethylethanesulfonanilide according to claim 23.

* * * * *